United States Patent [19]

Desgrandchamps et al.

[11] Patent Number: 5,701,746
[45] Date of Patent: Dec. 30, 1997

[54] METHOD TO REFRIGERATE A JACKET FOR KEEPING A TRANSPLANT COLD

[75] Inventors: Francois Desgrandchamps; Michel Eugene, both of Paris, France; Nico Girrens, Rodershausen; Fernand Muller, Ingeldorf, both of Luxembourg; Sylvia Spaniol, Merzig, Germany

[73] Assignee: Electrolux S.A.R.L., Vianden, Luxembourg

[21] Appl. No.: 624,518

[22] PCT Filed: Jun. 22, 1995

[86] PCT No.: PCT/EP95/02427

§ 371 Date: Jul. 25, 1996

§ 102(e) Date: Jul. 25, 1996

[87] PCT Pub. No.: WO96/01603

PCT Pub. Date: Jan. 25, 1996

[30] Foreign Application Priority Data

Jul. 12, 1994 [SE] Sweden ................................. 9402458

[51] Int. Cl.$^6$ ........................................................ F25D 25/00
[52] U.S. Cl. ........................................ 62/62; 62/78; 62/100
[58] Field of Search ............................ 62/78, 100, 269, 62/62

[56] References Cited

U.S. PATENT DOCUMENTS

| | | | |
|---|---|---|---|
| 3,628,537 | 12/1971 | Berndt et al. | 128/402 |
| 4,471,629 | 9/1984 | Toledo-Pereyra | 62/78 |
| 4,474,016 | 10/1984 | Winchell | 62/78 |
| 5,014,695 | 5/1991 | Benak et al. | 128/400 |
| 5,207,073 | 5/1993 | Maier-Laxhuber et al. | 62/269 |
| 5,475,983 | 12/1995 | Yamamoto et al. | 62/78 |

FOREIGN PATENT DOCUMENTS

| | | |
|---|---|---|
| 2497934 | 7/1982 | France . |
| 2949909 | 6/1981 | Germany . |

*Primary Examiner*—Ronald C. Capossela
*Attorney, Agent, or Firm*—Pearne, Gordon, McCoy & Granger LLP

[57] ABSTRACT

A jacket (10) for keeping a transplant (46) cold during the time the transplant in surgical way is connected to a receiver comprises a wall (12, 14) with a cavity (22) containing a frozen liquid, which melts under absorption of heat from the transplant. Before the transplant is placed in the jacket (10), the liquid, e.g. water, is frozen by being subjected to vacuum, vapour released from the liquid being absorbed by a substance, e.g. zeolite.

2 Claims, 1 Drawing Sheet

METHOD TO REFRIGERATE A JACKET FOR KEEPING A TRANSPLANT COLD

BACKGROUND OF THE INVENTION

The invention generally relates to a method for refrigerating a jacket, and, more specifically, to a method of using a refrigerated jacket to enclose and keep a transplant cold during the time the transplant is surgically installed within a recipient's body.

U.S. Pat. No. 5,014,695, discloses a jacket, which prevents a transplant, such as a kidney, from being heated, and thereby destroyed, by the body heat of the transplant recipient during the time it takes to connect the transplant surgically in the body of the recipient.

The known jacket is kept cold by a liquid the liquid, is circulated through the jacket via tubes connected to an outside source supplying cold liquid to the circulation. However with this jacket the tubes can obstruct access to the surgical site, and therefore impede the transplant procedure.

SUMMARY OF THE INVENTION

An object of the invention is to bring about a method of casting a transplant which makes it possible to enclose the transplant by a jacket having no tubes and ensuring that the transplant keeps an even and desired temperature during the time the transplant organ is surgically connected to the receiver.

According to the method the present invention, a jacket, which comprises a wall with a cavity containing a liquid and showing an opening to the cavity, is placed in a compartment. The compartment is evacuated so that the cavity is evacuated through the opening and the liquid within the cavity freezes.

BRIEF DESCRIPTION OF THE DRAWINGS

An embodiment of a jacket with an apparatus to evacuate a cavity of the jacket for carrying through the method according to the invention is described below with reference to the enclosed drawing figures, wherein.

DETAILED DESCRIPTION OF THE PREFERRED EMBODIMENT

Figure 1:
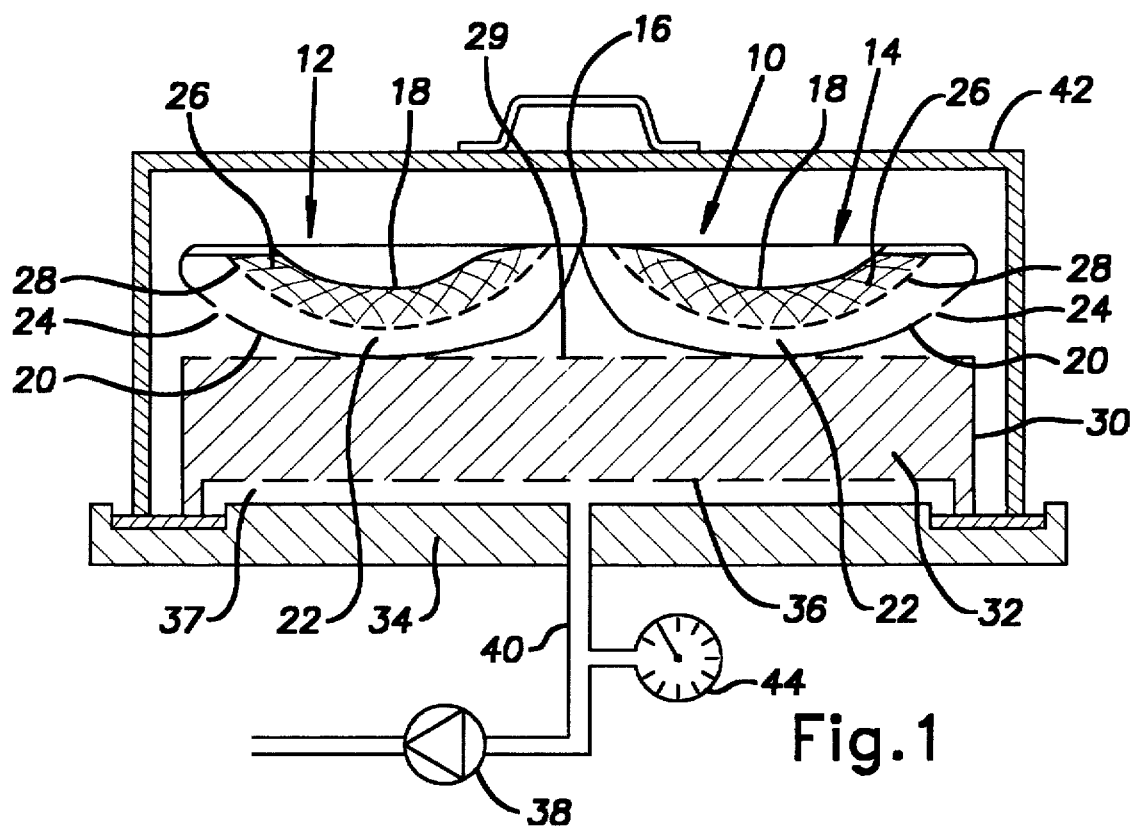
FIG. 1 in a sectional view shows the jacket in the apparatus for evacuating and thereby refrigerating the jacket and FIG. 2 in a sectional view shows a transplant enclosed by the jacket and ready to be surgically connected to a receiving patient.

With reference to the drawing figures, a jacket 10 consisting of two halves 12 and 14, respectively, which are turnably connected to each other around an axis 16, is illustrated. Each respective half includes an inner, rigid shell 18, e.g. of stainless steel, and an outer, rigid shell 20, e.g. of plastic. The shells 18,20 cooperate to define a cavity 22 therebetween which communicates with the surrounding atmosphere via an opening 24 in the outer shell 20. A liquid absorbing body 26 is disposed within the cavity 22 and kept in contact with the inner shell 18 by a perforated element 28. Each respective body 26 has been supplied with a determined quantity of liquid through the opening 24.

When the jacket 10 is to be refrigerated, the jacket is placed on a perforated upper surface 29 of a circular-cylindrical container 30 containing a substance 32 absorbing vapor from the liquid. The container 30 rests at its circumference on a plate 34, so a space 37 is defined between a lower perforated surface 36 of the container 30 and the plate. The space 37, communicates with a vacuum pump 38 via a conduit 40. A hood 42 is placed over the jacket and the container on the plate 34. The pump 38 is started, the respective cavity 22 being evacuated via the opening 24 and the substance 32. At a certain low pressure of the magnitude of 250–4000 Pa, which is readable on a manometer 44, the liquid in the body 26 begins to evaporate under heat rejection from the liquid, which thereby freezes, after which the pump 38 is stopped and surrounding air is let into the hood 42, so that it can be lifted off and make the jacket 10 available. It would require much energy and take long time for the vacuum pump 38 to pump away the vapour of the liquid. Therefore the container 30 with the substance 32 is arranged to absorb the vapour.

Figure 2:
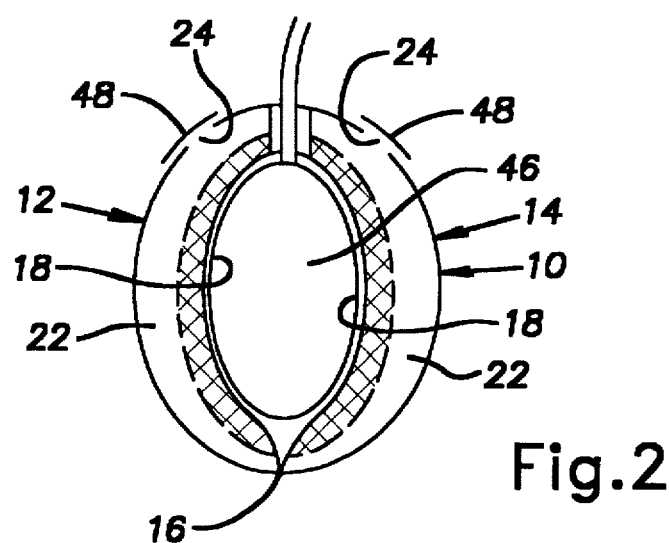

The transplant, e.g. a kidney 46, which shall be connected to a recipient and which is furnished in a cooled state, is now placed in the jacket 10 which is folded together around the transplant, as is shown in FIG. 2. The inner shells 18 have a form fitting to the shape of the transplant. The original, determined quantity of liquid in the bodies 26 is so large, that the liquid which has frozen in the bodies 26 will melt under absorption of heat via the shells 18 from the transplant at a constant temperature during the time it takes to surgically connect the transplant to the recipient.

The liquid can consist of water and the substance 32 of zeolite. By adding different substances to the water, different melting temperatures can be obtained.

It shall be pointed out that the principle made use of at the invention to freeze a liquid, e.g. water, by subjecting it to vacuum and thereby letting the vapour released from the liquid be absorbed by a substance, e.g. zeolite, is known per se through U.S. Pat. No. 5,207,073.

The jacket 10 is supplied containing said determined quantity of liquid in a sterile package, the respective opening 24 being sealed by a piece of tape 48, which is removed before the cavity 22 shall be evacuated. The piece of tape 48 is again brought over the opening 24, before the transplant shall be connected to the receiver.

The transplant can consist of another organ than a kidney, e.g. a heart, a lung or a liver.

We claim:

1. Method for refrigerating a jacket (10), said jacket being used to enclose and keep a transplant (46) cold while the transplant is surgically connected to a recipient, said jacket (10) having a wall with a cavity (22) containing a liquid and an opening (24) to the cavity, comprising the steps of placing the jacket in a compartment which is evacuated, evacuating the cavity through the opening and freezing the liquid.

2. Method according to claim 1, wherein vapor, which is liberated from the liquid during the evacuation, is absorbed by a substance (32) located in the compartment.

* * * * *

UNITED STATES PATENT AND TRADEMARK OFFICE
CERTIFICATE OF CORRECTION

PATENT NO. : 5,701,746
DATED : December 30, 1997
INVENTOR(S) : Desgrandchamps et al.

It is certified that error appears in the above-identified patent and that said Letters Patent is hereby corrected as shown below:

Column 1, line 11, delete "jacket, which" and insert --jacket which--.

Column 1, line 16, delete "liquid the liquid, is" and insert --liquid. The liquid is--.

Column 1, line 19, after "However" insert --,--.

Column 1, line 25, delete "casting" and insert --cooling--.

Column 1, line 29, delete "receiver" and insert --transplant recipient--.

Column 2, line 7, after "so" insert --that--.

Column 2, line 9, delete "37," and insert --37--.

Signed and Sealed this

Fourth Day of August, 1998

Attest:

BRUCE LEHMAN

*Attesting Officer*    *Commissioner of Patents and Trademarks*